United States Patent
Oda et al.

(10) Patent No.: US 6,242,622 B1
(45) Date of Patent: Jun. 5, 2001

(54) TRANSITION METAL COMPOUND, OLEFIN POLYMERIZATION CATALYST COMPONENT, OLEFIN POLYMERIZATION CATALYST AND PROCESS FOR PRODUCING OLEFIN POLYMER

(75) Inventors: Yoshiaki Oda; Takahiro Hino, both of Osaka; Hiroaki Katayama; Tsuyoshi Watanabe, both of Chiba, all of (JP)

(73) Assignee: Sumitomo Chemical Company, Ltd., Osaka (JP)

(*) Notice: Subject to any disclaimer, the term of this patent is extended or adjusted under 35 U.S.C. 154(b) by 0 days.

(21) Appl. No.: 09/348,046

(22) Filed: Jul. 6, 1999

(30) Foreign Application Priority Data

Jul. 8, 1998 (JP) ................................. 10-192866

(51) Int. Cl.$^7$ ............................ C07F 7/18; C08F 4/68; C08F 4/44
(52) U.S. Cl. .................. 556/11; 556/12; 556/52; 526/116; 526/161; 526/943; 502/153
(58) Field of Search ............. 556/11, 12, 52; 526/116, 161, 943

(56) References Cited

U.S. PATENT DOCUMENTS

| | | | |
|---|---|---|---|
| 4,542,199 | 9/1985 | Kaminsky et al. | 526/160 |
| 5,168,111 | 12/1992 | Canich | 526/160 |
| 5,703,187 | 12/1997 | Timmers | 526/282 |
| 6,066,704 | * 5/2000 | Katayama et al. | 526/127 |
| 6,084,046 | * 7/2000 | Johoji et al. | 526/339 |
| 6,084,048 | * 7/2000 | Hozumi et al. | 526/348.6 |
| 6,121,401 | * 9/2000 | Yamamoto et al. | 526/348.6 |

FOREIGN PATENT DOCUMENTS

| | | |
|---|---|---|
| 0 842 939 A1 | 5/1999 | (EP) . |
| 58-19309 | 2/1983 | (JP) . |
| 3-163088 | 7/1991 | (JP) . |
| 3-188092 | 8/1991 | (JP) . |

OTHER PUBLICATIONS

Abstract of Japan of JP 9176221 A, Jul. 8, 1997, Hino et al.
Abstract of Japan of 7126315 A, May 16, 1995, Watanabe et al.
Abstract of Japan of 4091095 A, Mar. 24, 1992, Inoue et al.

\* cited by examiner

*Primary Examiner*—Donald R. Wilson
*Assistant Examiner*—R. Harlan
(74) *Attorney, Agent, or Firm*—Pillsbury Winthrop LLP

(57) ABSTRACT

A specified transition metal compound having two transition metals and two cyclopentadiene type anion skeletone in tis molecule and said metals are linked through an atom of Group XVI of the Periodic Table of the Elements, and olefin polymerization catalyst component comprising said transition metal compound, an olefin polymerization catalyst comprising said transition metal compound, a specific organoaluminum compound, and a specific boron compound, and a process for producing an olefin polymer using said olefin polymerization catalyst.

5 Claims, 1 Drawing Sheet

(A) Transition Metal Component $M^1$: 4th Group transition Metal Atom,
A: 16th Group Atom, J: 14th Group Atom
$Cp^1$: Group having Cyclopentadiene Anion Type Skeleton, $X^2$: 16th Group Atom (B) Organometallic Component Organoaluminum and/or Aluminoxane (C) Third Component
Boron Compound → Olefin Polymer

TRANSITION METAL COMPOUND, OLEFIN POLYMERIZATION CATALYST COMPONENT, OLEFIN POLYMERIZATION CATALYST AND PROCESS FOR PRODUCING OLEFIN POLYMER

BACKGROUND OF THE INVENTION

1. Field of the Invention

The present invention relates to a transition metal compound useful as an olefin polymerization catalyst component, an olefin polymerization catalyst, using said transition metal compound and process for producing an olefin polymer using said olefin polymerization catalyst with a high activity.

2. Description of the Related Art

Many processes for producing an olefin polymer with a metallocene complex have been already reported. For example, a process for producing an olefin polymer with a metallocene complex and an aluminoxane is reported in Japanese Patent Publication (Kokai) No. 58-19306. The metallocene complex disclosed therein is a complex having only one transition metal atom in its molecule.

It is disclosed in Japanese Patent Publication (Kokai) No. 4-91095 to use a metallocene complex having a structure in which two transition metal atoms are contained in its molecule and two η'-cyclopentadienyl groups coordinate on each on each of the transition metal atoms, as an olefin polymerization catalyst component.

However, when these metallocene complexes having the structure in which two η'-cyclopentadienyl groups coordinate on one transition metal atom are used as the olefin polymerization catalyst component, there are problems that the molecular weight of an olefin polymer obtained is low and the comonomer reaction rate in copolymerization is low, and the more improvement of activity has been desired from an industrial viewpoint.

Although metallocene complexes in which two transition metal atoms are contained in its molecule and only one $\eta^5$-cyclopentadienyl group coordinates on each of transition metal atoms are disclosed in Japanese Patent Publication (Kokai) Nos. 3-163088 and 3-188092, they are complexes having a peculiar structure in which excessive anionic ligands against the valence number of a transition metal atom are combined, and its polymerization activity is not confirmed.

Although a metallocene complex in which two transition metal atoms are contained in its molecule and only one $\eta^5$-cyclopentadienyl group coordinates per one transition metal atom is disclosed in Japanese Patent Publication (Kokai) No. 7-126315, it is a complex having a structure in which those two $\eta^5$-cyclopentadienyl groups are linked, and there are problems in that the olefin polymerization catalyst using it as a catalyst component has low comonomer reaction rate in copolymerization and the melting point of a copolymer improvement of activity has been desired from an industrial viewpoint.

SUMMARY OF THE INVENTION

Under these situations, the objects of the present invention are to provide a transition metal compound useful as a highly active olefin polymerization catalyst component at an efficient reaction temperature in the industrial process of important olefin polymerization from an industrial view point, and to provide a highly active olefin polymerization catalyst using said transition metal compound and a process for producing an olefin polymer using said olefin polymerization catalyst.

In order to attain the above-mentioned objects, the present inventors have intensively studied a process for producing an olefin polymer using a metallocene transition metal compound, in particular, a mono cyclopentadienyl transition metal compound as one of catalyst components, and have thus completed the present invention.

The present invention relates to a transition metal compound represented by the general formula [I] or [II] described below, an olefin polymerization catalyst component comprising said transition metal compound, an olefin polymerization catalyst prepared by a process comprising contacting a transition metal compound selected from the group consisting of transition metal compounds represented by the general formulas [I] and [II], and [(B) described below and/or (C)] described below, and a process for producing an olefin polymer with said olefin polymerization catalyst.

[I]

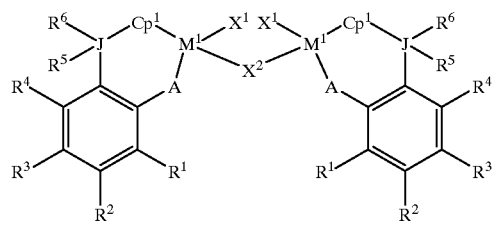

[II]

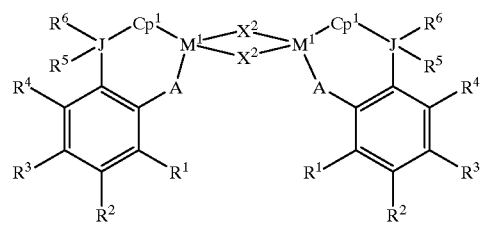

(wherein $M^1$ indicates a transition metal atom of the Group IV of the Periodic Table of the Elements; A indicates an atom of the Group XVI of the Periodic Table of the Elements; J indicates an atom of the Group XIV of the Periodic Table of the Elements; $Cp^1$ indicates a group having a cyclopentadiene type anion skeleton; each of $X^1$, $R^1$, $R^2$, $R^1$, $R^4$, $R^5$ and $R^6$ independently indicates a hydrogen atom, a halogen atom, an alkyl group, an aralkyl group, an aryl group, a substituted silyl group, an alkoxy group, an aralkyloxy group, an aryloxy group or a di-substituted amino group; $X^2$ indicates an atom of Group XVI of the Periodic Table of the Elements; $R^1$, $R^2$, $R^3$, $R^4$, $R^5$ and $R^6$ may be optionally combined with each other to form a ring; and a plural number of $M^1$, A, J, $Cp^1$, $X^1$, $X^2$, $R^1$, $R^2$, $R^3$, $R^4$, $R^5$ and $R^6$ may be respectively the same or different.)

(B) at least one aluminum compound selected from (B1) to (B3) described below:
 (B1) an organoaluminum compound indicated by the general formula $E^1{}_a AlZ_{3-a}$;
 (B2) a cyclic aluminoxane having a structure indicated by the general formula $\{-Al(E^2)-O-\}_b$; and
 (B3) a linear aluminoxane having a structure indicated by the general formula $E^3\{-Al(E^3)-O-\}_c AlE^3{}_2$
 (wherein each of $E^1$, $E^2$ and $E^3$ is a hydrocarbon group, and all of $E^1$, all of $E^2$ and all of $E^3$ may be the same or different; z represents a hydrogen atom or a halogen atom; and all of z may be the same or different; a represents a number satisfying an expression of $0 < a \leq 3$; b represents an integer of 2 or more; and c represents an integer of 1 or more).

(C) any one of boron compounds of (C1) to (C3) described below:

(C1) a boron compound represented by the general formula $BQ^1Q^2Q^3$;

(C2) a boron compound represented by the general formula $G^+(BQ^1Q^2Q^3Q^4)^-$; and (C3) a boron compound represented by the general formula $(L-H)^+(BQ^1Q^2Q^3Q^4)^-$ (wherein B is a boron atom in the trivalent valence state; $Q^3$ to $Q^4$ are a halogen atom, a hydrocarbon group, a halogenated hydrocarbon group, a substituted silyl group, an alkoxy group or a di substituted amino group which may be the same or different; $G^+$ is an inorganic or organic cation; L is a neutral Lewis base; and $(L H)^+$ is a Brønsted acid).

DETAILED DESCRIPTION OF THE INVENTION

Figure 1:
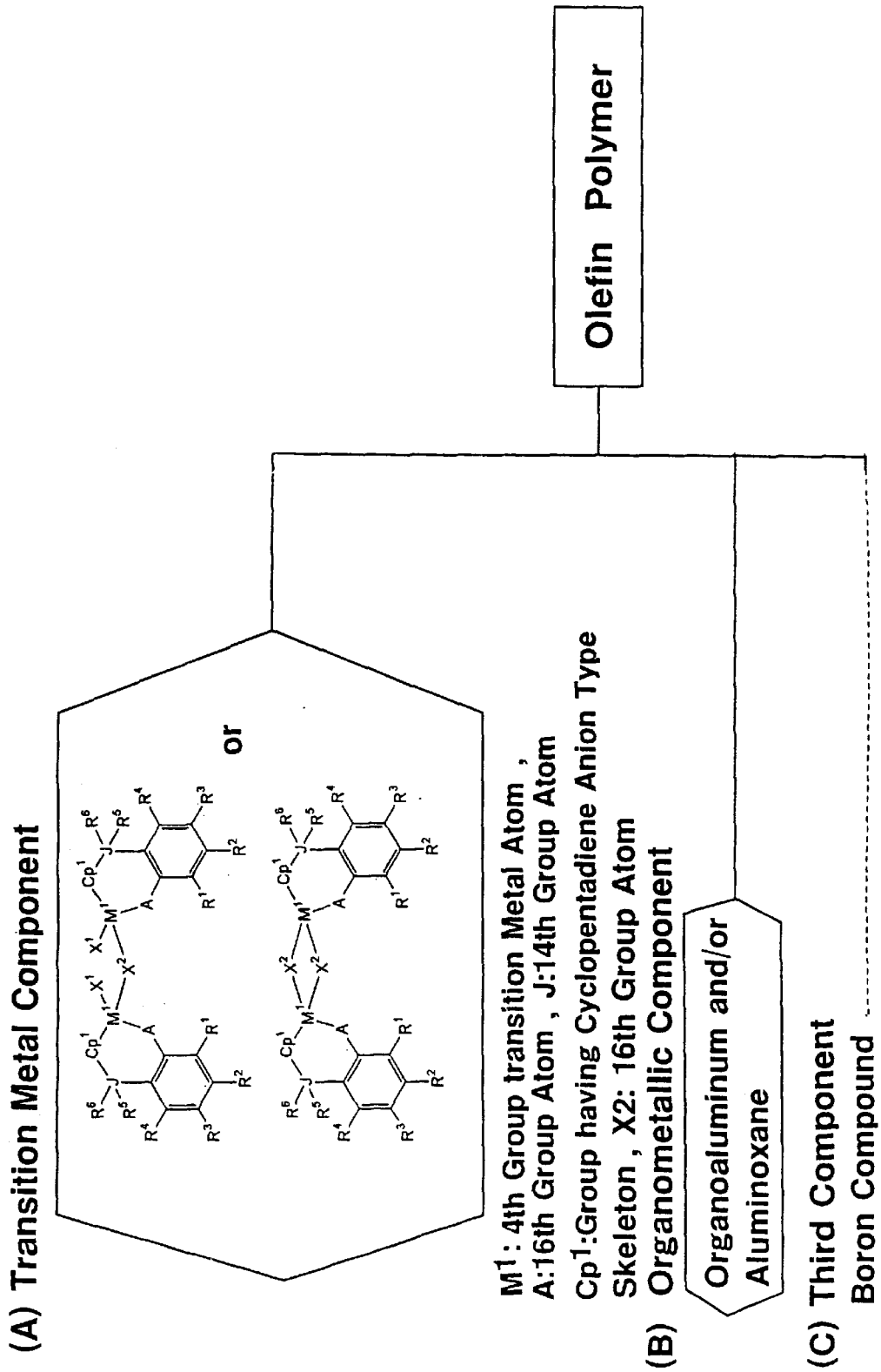
FIG. 1 shows a flow chart for assisting the understanding of the present invention. The flow chart is a typical example of the mode of operation of the present invention, but the present invention is not limited thereto.

The present invention is further illustrated in detail below.

(A) Transition Metal Compound

In the general formula [I] or [II], the transition metal atom represented by $M^1$ indicates a transition metal element of the Group IV of the Periodic Table of the Elements (Revised edition of IUPAC Inorganic Chemistry Nomenclature 1989), and examples thereof include a titanium atom, a zirconium atom, a hafnium atom and the like. A titanium atom or a zirconium atom is preferable.

Examples of the atom of the Group XVI of the Periodic Table of the Elements indicated as A in the general formula [I] or [II] include an oxygen atom, a sulfur atom, a selenium atom and the like, and an oxygen atom is preferable.

Examples of the atom of the Group XIV of the Periodic Table of the Elements indicated as J in the general formula [I] or [II] include a carbon atom, a silicon atom, a germanium atom and the like, and a carbon atom or a silicon atom is preferable.

Examples of the group having a cyclopentadiene type anion skeleton indicated as the substituent group, $Cp^1$, include an $\eta^5$-(substituted)cyclopentadienyl group, an $\eta^5$-(substituted)indenyl group, an $\eta^5$ (substituted) fluorenyl group and the like. Specific examples include an $\eta^5$-cyclopentadienyl group, an $\eta^5$-methylcyclopentadienyl group, an $\eta^5$-dimethylcyclopentadienyl group, an $\eta^5$-trimethylcyclopentadienyl group, an $\eta^5$-tetramethylcyclopentadienyl group, an $\eta^5$-ethylcyclopentadienyl group, an $\eta^5$-n-propylcyclopentadienyl group, an $\eta^5$-isopropylcyclopentadienyl group, an $\eta^5$-n-butylcyclopentadienyl group, an $\eta^5$-sec-butylcyclopentadienyl group, an $\eta^5$-tert-butylcyclopentadienyl group, an $\eta^5$-n-pentylcyclopentadienyl group, an $\eta^5$-neopentylcyclopentadienyl group, an $\eta^5$-n-hexylcyclopentadienyl group, an $\eta^5$-n-octylcyclopontadienyl group, an $\eta^5$-phenylcyclopentadienyl group, an $\eta^5$-napthylcyclopentadienyl group, an $\eta^5$-trimethylsilylcyclopentadienyl group, an $\eta^5$-triethylsilylcyclopentadienyl group, an $\eta^5$-tert-butyldimethylsilylcyclopentadienyl group, an $\eta^5$-indenyl group, an $\eta^5$-methylindenyl group, an $\eta^5$-dimethylindenyl group, an $\eta^5$-ethylindenyl group, an $\eta^5$-n-propylindenyl group, an $\eta^5$-isopropylindenyl group, an $\eta^5$-n-butylindenyl group, an $\eta^5$-sec butylindenyl group, an $\eta^5$-tert-butylindenyl group, an $\eta^5$-n-pentylindenyl group, an $\eta^5$-neopentylindenyl group, an $\eta^5$-n hexylindenyl group, an $\eta^5$-n-octylindenyl group, an $\eta^5$-n-decylindenyl group, an $\eta^5$-phenylindenyl group, an $\eta^5$-mothylphenylindenyl group, an $\eta^5$-naphthylindenyl group, an $\eta^5$-trimethylsilylindenyl group, an $\eta^5$-triethylsilylindenyl group, an $\eta^5$-tert-butyldimethylsilylindenyl group, an $\eta^5$-tetrahydroindenyl group, an $\eta^5$-fluorenyl group, an $\eta^5$-methylfluorenyl group, an $\eta^5$-dimethylfluorenyl group, an $\eta^5$-ethylfluorenyl group, an $\eta^5$-diethylfluorenyl group, an $\eta^5$ n-propylfluorenyl group, an $\eta^5$-di-n-propylfluorenyl group, an $\eta^5$-isopropylfluorenyl group, an $\eta^5$-diisopropylfluorenyl group, an $\eta^5$-n-butylfluorenyl group, an $\eta^5$-sec-butylfluorenyl group, an $\eta^5$-tert-butylfluorenyl group, an $\eta^5$-di-n-butylfluorenyl group, an $\eta^5$-di-sec-butylfluorenyl group, an $\eta^5$-di-tert-butylfluorenyl group, an $\eta^5$-n-pentylfluorenyl group, an $\eta^5$-neopentylfluorenyl group, an $\eta^5$ n-hexylfluorenyl group, an $\eta^5$-n-octylfluorenyl group, an $\eta^5$-n-decylfluorenyl group, an $\eta^5$-n-dodecylfluorenyl group, an $\eta^5$-phenylfluorenyl group, an $\eta^5$-dipehnylfluorenyl group, an $\eta^5$-methylphenylfluorenyl group, an $\eta^5$-naphthylfluorenyl group, an $\eta^5$-trimethylsilylfluorenyl group, an $\eta^5$-bis-trimethylsilylfluorenyl group, an $\eta^5$-triethylsilylfluorenyl group, an $\eta^5$-tert-butyldimethylsilylfluorenyl group and the like. An $\eta^5$-cyclopentadienyl group, an $\eta^5$-methylcyclopentadionyl group, an $\eta^5$-tert-butylcyclopentadienyl group, an $\eta^5$-tetramethylcyclopentadienyl group, an $\eta^5$-indenyl group or an $\eta^5$-fluorenyl group is preferable.

As the halogen atom in the substituent, $X^1$, $R^1$, $R^2$, $R^3$, $R^4$, $R^5$ or $R^6$, a fluorine atom, a chlorine atom, a bromine atom, and an iodine atom are illustrated. A chlorine atom or a bromine atom is preferable and a chlorine atom is more preferable.

As the alkyl group in the substituent, $X^1$, $R^1$, $R^2$, $R^3$, $R^4$, $R^5$ or $R^6$, an alkyl group having 1 to 20 carbon atoms is preferred, and examples includes a methyl group, an ethyl group, a n-propyl group, an isopropyl group, a n-butyl group, a sec-butyl group, a tert-butyl group, a n-pentyl group, a neopentyl group, a sec-amyl group, a n-hexyl group, a n-octyl group, a n-decyl group, a n-dodecyl group, a n-pentadecyl group, a n-eicosyl group and the like, and a methyl group, an ethyl group, an isopropyl group, a tert-butyl group or a sec-amyl group is more preferable.

All of these alkyl groups may be substituted with a halogen atom such as a fluorine atom, a chlorine atom, a bromine atom or an iodine atom. Examples of the alkyl group having 1 to 20 carbon atoms which is substituted with the halogen atom, include a fluoromethyl group, a difluoromethyl group, a trifluoromethyl group, a chloromethyl group, a dichloromethyl group, a trichloromethyl group, a bromomethyl group, a dibromomethyl group, a tribomomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, pentachloroethyl group, a bromoethyl group, a dibromoethyl group, a tribromoethyl group, a tetrabromoethyl group, pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group, a perbromoeicosyl group and the like.

Further, all of these alkyl groups may be partially substituted with an alkoxy group such as a methoxy group, an ethoxy group or the like, an aryloxy group such as a phenoxy group or the like or an aralkyloxy group such as a benzyloxy group or the like, etc.

As the aralkyl group in the substituent, $X^1$, $R^1$, $R^2$, $R^3$, $R^4$, $R^5$ or $R^6$, an aralkyl group having 7 to 20 carbon atoms is preferable, and examples thereof include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-timethylphenyl)methyl group, a (2,3,5-timethylphenyl)methyl group, a (2,3,6-timethylphenyl)methyl group, a (3,4,5-timethylphenyl)methyl group, a (2,4,6-timethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-dodecylphenyl)methyl group, a naphthylmethyl group, an anthracenylmethyl group an the like, and a benzyl group is more preferable.

All of these aralkyl groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

As the aryl group in the substituent, $X^1$, $R^1$, $R^2$, $R^3$, $R^4$, $R^5$ or $R^6$, an aryl group having 6 to 20 carbon atoms is preferable, and examples thereof include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 2,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group, an anthracenyl group and the like, and a phenyl group is more preferable.

All of these aryl groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like or an aralkyloxy group such as a benzyloxy group or the like, etc.

The substituted silyl group in the substituent, $X^1$, $R^1$, $R^2$, $R^3$, $R^4$, $R^5$ or $R^6$ is a silyl group substituted with a hydrocarbon group, and examples of the hydrocarbon group include alkyl groups having 1 to 10 carbon atoms such as a methyl group, an ethyl group, a n-propyl group, an isopropyl group, a n-butyl group, a sec-butyl group, a tert-butyl group, an isobutyl group, a n-pentyl group, a n-hexyl group, a cyclohexyl group and the like, and aryl groups such as a phenyl group and the like, etc. Examples of such substituted silyl group having 1 to 20 carbon atoms include monosubstituted silyl groups having 1 to 20 carbon atoms such as a methylsilyl group, an ethylsilyl group, a phenylsilyl group and the like; di-substituted silyl groups having 2 to 20 carbon atoms such as a dimethylsilyl group, a diethylsilyl group, a diphenylsilyl group and the like; and tri-substituted silyl groups having 3 to 20 carbon atoms such as a trimethylsilyl group, a triethylsilyl group, a tri-n-propylsilyl group, a triisopropylsilyl group, a tri-n-butylsilyl group, a tri-sec-butylsilyl group, a tri-tert-butylsilyl group, a tri-isobutylsilyl group, a tert-butyl dimethylsilyl group, a tri-n-pentylsilyl group, a tri-n-hexylsilyl group, a tricyclohexylsilyl group, a triphenylsilyl group and the like, and a trimethylsilyl group, a tert-butyldimethylsilyl group or a triphenylsilyl group is preferable.

All of the hydrocarbon groups of these substituted silyl groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

As the alkoxy group in the substituent $X^1$, $R^1$, $R^2$, $R^3$, $R^4$, $R^5$ or $R^6$, an alkoxy group having 1 to 20 carbon atoms is preferable, and examples thereof include a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group, a n-eicosoxy group and the like, and a methoxy group, an ethoxy group or a tert-butoxy group is preferable.

All of these alkoxy groups may be partially substituted with a halogen atom such as a fluorine atom, a chlorine atom, a bromine atom, an iodine atom or the like, an alkoxy group such as a methoxy group, an ethoxy group or the like, an aryloxy group such as a phenoxy group or the like or an aralkyloxy group such as a benzyloxy group or the like, etc.

As the aralkyloxy group in the substituent, $X^2$, $R^1$, $R^2$, $R^3$, $R^4$, $R^5$ or $R^6$, an aralkyloxy group having 7 to 20 carbon atoms is preferable, and examples thereof include a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a naphthylmethoxy group, an anthracenylmethoxy group and the like, and a benzyloxy group is more preferable.

All of these aralkyloxy groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

As the aryloxy group in the substituent, $X^1$, $X^2$, $R^1$, $R^2$, $R^3$, $R^4$, $R^5$ or $R^6$, an aryloxy group having 6 to 20 carbon atoms is preferable, and examples thereof include a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert butylphenoxy group, a n-hexylphenoxy group, a n-octylphenoxy group, a n-decylphenoxy group, a n-tetradecylphenoxy group, a naphthoxy group, an anthracenoxy group and the like.

All of these aryloxy groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

The di-substituted amino group in the substituent, $X^1$, $R^1$, $R^2$, $R^3$, $R^4$, $R^5$ or $R^6$ is an amino group substituted with two hydrocarbon groups, and examples of the hydrocarbon group include alkyl groups having 1 to 10 carbon atoms such as a methyl group, an ethyl group, a n-propyl group, an isopropyl group, a n-butyl group, a sec-butyl group, a tert-butyl group, an isobutyl group, a n-pentyl group, a n-hexyl group, a cyclohexyl group and the like; aryl groups having 6 to 10 carbon atoms such as a phenyl group and the like; aralkyl groups having 7 to 10 carbon atoms, etc. Examples of such di-substituted amino group substituted with the hydrocarbon group having 1 to 10 carbon atoms include a dimethylamino group, a diethylamino group, a di-n-propylamino group, a diisopropylamino group, a di-n-butylamino group, a di-sec-butylamino group, a di-tert-butylamino group, a di-isobutylamino group, a tert-butylisopropylamino group, a di-n-hexylamino group, a di-n-octylamino group, a di-n-decylamino group, a diphenylamino group, a bistrimethylsilylamino group, a bis-tert-butyldimethylsilylamino group and the like, and a dimethylamino group or an diethylamino group is preferable.

All of these di-substituted amino groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

The substituent, $R^1$, $R^2$, $R^3$, $R^4$, $R^5$ or $R^6$ may be optionally combined with each other to form a ring.

Each of $R^1$ is preferably an alkyl group, an aralkyl group, an aryl group or a substituted silyl group, independently.

Each of $X^1$ is preferably a halogen atom, an alkyl group, an aralkyl group, an alkoxy group, an aryloxy group or a di-substituted amino group, independently. An alkoxy group is more preferable.

Examples of the atom of Group XVI of the Periodic Table of the Elements indicated as $X^2$ in the general formula [I] or [II] include an oxygen atom, a sulfur atom, a selenium atom and the like, and an oxygen atom is preferable.

Examples of such transition metal compound [I] include $\mu$-oxobis{isopropylidene($\eta^5$-cyclopentadienyl)(2-phenoxy)titanium chloride}, $\mu$-oxobis{isopropylidene($\eta^5$-cyclopentadienyl)(2-phenoxy)titanium methoxide}, $\mu$-oxobis{isopropylidene($\eta^5$-cyclopentadienyl)(3-tert-butyl-5-methyl-2-phenoxy)titanium chloride}, $\mu$-oxobis{isopropylidene($\eta^5$-cyclopentadienyl)(3-tert-butyl-5-methyl-2-phenoxy)titanium methoxide}, $\mu$-oxobis{isopropylidene($\eta^5$-methylcyclopentadienyl)(2-phenoxy)titanium chloride}, $\mu$-oxobis{isopropylidene($\eta^5$-methylcyclopentadienyl)(2-phenoxy)titanium methoxide}, $\mu$-oxobis{isopropylidene($\eta^5$-methylcyclopentadienyl)(3-tert-butyl-5-methyl-2-phenoxy)titanium chloride}, $\mu$-oxobis{isopropylidene($\eta^5$-methylcyclopentadienyl)(3-tert-butyl-5-methyl-2-phenoxy)titanium methoxide}, $\mu$-oxobis{isopropylidene ($\eta^5$-tetramethylcyclopentadienyl)(2-phenoxy)titanium chloride}, $\mu$-oxobis{isopropylidene($\eta^5$-tetramethylcyclopentadienyl)(2-phenoxy)titanium methoxide}, $\mu$-oxobis{isopropylidene($\eta^5$-tetramethylcyclopentadienyl)(3-tert-butyl-5-methyl 2-phenoxy)titanium chloride}, $\mu$-oxobis{isopropylidene($\eta^5$-tetramethylcyclopentadienyl)(3-tert-butyl-5-methyl-2-phenoxy)titanium methoxide}, $\mu$-oxobis{dimethylsilylene ($\eta^5$-cyclopentadienyl)(2-phenoxy)titanium chloride}, $\mu$-oxobis{dimethylsilylene($\eta^5$-cyclopentadienyl)(2-phenoxy)titanium methoxide}, $\mu$-oxobis{dimethylsilylene ($\eta^5$-cyclopentadienyl)(3-tert-butyl-5-methyl-2-phenoxy)titanium chloride}, $\mu$-oxobis{dimethylsilylene($\eta^5$-cyclopentadienyl)(3-tert-butyl-5-methyl-2-phenoxy)titanium methoxide}, $\mu$-oxobis{dimethylsilylene($\eta^5$-methylcyclopentadienyl)(2-phenoxy)titanium chloride}, $\mu$-oxobis{dimethylsilylene($\eta^5$-methylcyclopentadienyl)(2-phenoxy)titanium methoxide}, $\mu$-oxobis{dimethylsilylene ($\eta^5$-methylcyclopentadienyl)(3-tert-butyl-5-methyl-2-phenoxy)titanium chloride}, $\mu$-oxobis{dimethylsilylene($\eta^5$-methylcyclopentadienyl)(3-tert-butyl-5-methyl-2-phenoxy)titanium methoxide}, $\mu$-oxobis{dimethylsilylene($\eta^5$-tetramethylcyclopentadienyl)(2-phenoxy)titanium chloride}, $\mu$-oxobis{dimethylsilylene($\eta^5$-tetramethylcyclopentadienyl)(2-phenoxy)titanium methoxide}, $\mu$-oxobis{dimethylsilylene($\eta^5$-tetramethylcyclopentadienyl)(3-tert-butyl-5-methyl-2-phenoxy)titanium chloride}, $\mu$-oxobis{dimethylsilylene($\eta^5$-tetramethylcyclopentadienyl)(3-tert-butyl-5-methyl-2-phenoxy)titanium methoxide} and the like.

Examples of such transition metal compound [II] include di-$\mu$-oxobis{isopropylidene($\eta^5$-cyclopentadienyl)(2-phenoxy)titanium}, di-$\mu$-oxobis{isopropylidene($\eta^5$- cyclopentadienyl)(3-tert-butyl-5-methyl-2-phenoxy) titanium}, di-μ-oxobis{isopropylidene($\eta^5$-methylcyclopentadienyl)(2-phenoxy)titanium}, di-μ-oxobis{isopropylidene($\eta^5$-methylcyclopentadienyl)(3-tert-butyl-5-methyl-2-phenoxy)titanium}, di-μ-oxobis{isopropylidene($\eta^5$-tetramethylcyclopentadienyl)(2-phenoxy)titanium}, di-μ-oxobis{isopropylidene($\eta^5$-tetramethyl cyclopentadienyl)(3-tert-butyl-5-methyl-2-phenoxy)titanium}, di-μ oxobis[dimethylsilylene ($\eta^5$-cyclopentadienyl)(2-phenoxy)titanium], di-μ-oxobis{dimethylsilylene($\eta^5$-cyclopentadienyl)(3-tert-butyl-5-methyl-2-phenoxy)titanium}, di-μ-oxobis{dimethylsilylene($\eta^5$-methylcyclopentadienyl)(2-phenoxy)titanium}, di-μ-oxobis{dimethylsilylene($\eta^5$-methylcyclopentadienyl)(3-tert-butyl-5-methyl-2-phenoxy) titanium}, di-μ-oxobis{dimethylsilylene($\eta^5$-tetramethylcyclopentadienyl)(2-phenoxy)titanium}, di-μ-oxobis{dimethylsilylene($\eta^5$-tetramethylcyclopentadienyl)(3-tert-butyl-5-methyl-2-phenoxy)titanium} and the like.

The transition metal compound represented by the general formula [I] or [II] can be produced, for example, by reacting a transition metal compound obtained according to the method described in the WO 97/03992 with 0.5-fold by mole or 1-fold by mole of water. Wherein a method of directly reacting a transition metal compound with a required amount of water, a method of charging a transition metal compound in a solvent such as a hydrocarbon containing a required amount of water, or the like, a method of charging a transition metal compound in a solvent such as a dry hydrocarbon or the like and further flowing an inert gas containing a required amount of water, or the like, etc. can be adopted.

(B) Aluminum Compound

The aluminum compound (B) used in the present invention is at least one organoaluminum compound selected from (B1) to (B3) described below:

(B1) an organoaluminum compound indicated by the general formula $E^1_a AlZ_{3-a}$;

(B2) a cyclic aluminoxane having a structure indicated by the general formula $\{-Al(E^2)-O-\}_b$; and (B3) a linear aluminoxane having a structure indicated by the general formula $E^3\{-Al(E^3)-O-\}_c AlE^3_2$ (wherein each of $E^1$, $E^2$ and $E^3$ is a hydrocarbon group; all of $E^1$, all of $E^2$ and all of $E^3$ may be the same or different; Z represents a hydrogen atom or a halogen atom; all of Z may be the same or different; a represents a number satisfying an expression of $0<a\leq 3$; b represents an integer of 2 or more and c represents an integer of 1 or more).

As the hydrocarbon group in $E^1$, $E^2$ or $E^3$, a hydrocarbon group having 1 to 8 carbon atoms is preferable and an alkyl group is more preferable.

Specific examples of the organoaluminum compound (B1), indicated by the general formula $E^1_a AlE_{3-a}$ include trialkylaluminums such as trimethylaluminum, triethylaluminum, tri-n-propylaluminum, triisopropylaluminum, triisobutylaluminum, tri-n-hexylaluminum and the like; dialkylaluminum chlorides such as dimethylaluminum chloride, diethylaluminum chloride, di-n-propylaluminum chloride, diisopropylaluminum chloride, diisobutylaluminum chloride, di-n-hexylaluminum chloride and the like; alkylaluminum dichlorides such as methylaluminum dichloride, ethylaluminum dichloride, n-propylaluminum dichloride, isopropylaluminum dichloride, isobutylaluminum dichloride, n-hexylaluminum dichloride and the like; and dialkylaluminum hydrides such as dimethylaluminum hydride, diethylaluminum hydride, di-n-propylaluminum hydride, diisopropylaluminum hydride, diisobutylaluminum hydride, di-n-hexylaluminum hydride and the like, etc.

Trialkylaluminum is preferable and triethylaluminum or triisobutylaluminum is more preferable.

Specific examples of $E^2$ and $E^3$ in the cyclic aluminoxane (B2) having a structure indicated by the general formula $\{-Al(E^2)-O-\}_b$ and the linear aluminoxane(B3) having a structure indicated by the general formula $E^3\{-Al(E^3)-O-\}_c AlE^3_2$ include alkyl groups such as a methyl group, an ethyl group, a n-propyl group, an isopropyl group, a n-butyl group, an isobutyl group, a n-pentyl group, a neopentyl group and the like. b is an integer of 2 or more, and c is an integer of 1 or more. Preferably, each of $E^2$ and $E^3$ is a methyl group or an isobutyl group, b is 2 to 40 and c is 1 to 40.

The above-mentioned aluminoxane is prepared by various methods. The method is not specifically limited, and the aluminoxane may be prepared according to publicly known processes.

For example, the aluminoxane is prepared by contacting a solution of a trialkylaluminum (e.g. trimethylaluminum or the like) dissolved in a suitable organic solvent (e.g. benzene, an aliphatic hydrocarbon or the like) with water. Further, there is exemplified a process for preparing the aluminoxane by contacting a trialkylaluminum (e.g. trimethylaluminum, etc.) with a metal salt containing crystal water (e.g. copper sulfate hydrate, etc.).

(C) Boron Compound

As the boron compound (C) in the present invention, any one of the boron compound (C1) represented by the general formula $BQ^1Q^2Q^3$, the boron compound (C2) represented by the general formula $G^+(BQ^1Q^2Q^3Q^4)^-$ and the boron compound (C3) represented by the general formula $(L-H)^+(BQ^1Q^2Q^3Q^4)^-$ can be used.

In the boron compound (C1) represented by the general formula $BQ^1Q^2Q^3$, B represents a boron atom in the trivalent valence state; $Q^1$ to $Q^3$ are respectively a halogen atom, a hydrocarbon group, a halogenated hydrocarbon group, a substituted silyl group, an alkoxy group or a di-substituted amino group and they may be the same or different. Each of $Q^1$ to $Q^3$ is preferably a halogen atom, a hydrocarbon group having 1 to 20 carbon atoms, a halogenated hydrocarbon group having 1 to 20 carbon atoms, a substituted silyl group having 1 to 20 carbon atoms, an alkoxy group having 1 to 20 carbon atoms or a di-substituted amino group having 2 to 20 carbon atoms, and each of more preferable $Q^1$ to $Q^3$ is a halogen atom, a hydrocarbon group having 1 to 20 carbon atoms or a halogenated hydrocarbon group having 1 to 20 carbon atoms. Each of the more preferable $Q^1$ to $Q^2$ is a fluorinated hydrocarbon group having 1 to 20 carbon atoms which contains at least one fluorine atom, and in particular, each of $Q^1$ to $Q^4$ is preferably a fluorinated aryl group having 6 to 20 carbon atoms which contains at least one fluorine atom.

Specific examples of the compound (Ci) include tris (pentafluorophenyl)borane, tris(2,3,5,6-tetrafluorophenyl) borane, tris(2,3,4,5-tetrafluorophenyl)borane, tris(3,4,5-trifluorophenyl)borane, tris(2,3,4-trifluorophenyl)borane, phenylbis(pentafluorophenyl)borane and the like, and tris (pentafluorophenyl)borane is most preferable.

In the boron compound (C2) represented by the general formula $G^+(BQ^1Q^2Q^3Q^4)^-$, $G^+$ is an inorganic or organic cation; B is a boron atom in the trivalent valence state; and $Q^1$ to $Q^4$ are the same as defined in $Q^1$ to $Q^3$ in the above-mentioned (C1).

Specific examples of $G^+$ as the inorganic cation in the compound represented by the general formula $G^+(BQ^1Q^2Q^3Q^4)^-$ include a ferrocenium cation, an alkyl-substituted ferrocenium cation, a silver cation and the like, and the $G^+$ as the organic cation includes a triphenylmethyl cation and the like. $G^+$ is preferably a carbonium cation, and a triphenylmethyl cation is particularly preferred. As the $(BQ^1Q^2Q^3Q^4)$, tetrakis(pentafluorophenyl)borate, tetrakis (2,3,5,6-tetrafluorophenyl)borate, tetrakis(2,3,4,5 tetrafluorophenyl)borate, tetrakis(3,4,5-trifluorophenyl) borate, tetrakis(2,3,4-trifluorophenyl)borate, phenyltris (pentafluorophenyl)borate, tetrakis(3,5-bistrifluoromethylphenyl)borate and the like are mentioned.

These specific combinations include ferrocenium tetrakis (pentafluorophenyl)borate, 1,1'-dimethylferrocenium tetrakis(pentafluorophenyl) borate, silver tetrakis (pentafluorophenyl)borate, triphenylmethyl tetrakis (pentafluorophenyl)borate, triphenylmethyl tetrakis(3,5-bistrifluoromethylphenyl)borate and the like, and triphenylmethyl tetrakis(pentafluorophenyl)borate is most preferable.

Further, in the boron compound (C3) represented by the formula $(L—H)^+(BQ^1Q^2Q^3Q^4)^-$, L is a neutral Lewis base; $(L—H)^+$ is a Brønsted acid; B is a boron atom in the trivalent valence state; and $Q^1$ to $Q^4$ are the same as $Q^1$ to $Q^3$ in the above-mentioned Lewis acid (C1).

Specific examples of $(L—H)^+$ as the Brønsted acid in the compound represented by the formula $(L—H)^+$ $(BQ^1Q^2Q^3Q^4)$ include a trialkyl-substituted ammonium, an N,N-dialkylanilinium, a dialkylammonium, a triarylphosphonium and the like, and examples of $(BQ^1Q^2Q^3Q^4)^-$ include those as previously described.

These specific combinations include triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl) borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl) phosphonium tetrakis(pentafluorophenyl)borate, tri (dimethylphenyl)phosphonium tetrakis(pentafluorophenyl) borate and the like, and tri(n-butyl)ammonium tetrakis (pentafluorophenyl)borate or N,N-dimethylanilinium tetrakis(pentafluorophenyl)borate is most preferable.

[Polymerization of Olefin]

In the present invention, the olefin polymerization catalyst is prepared by a process comprising contacting the transition metal compound (A) represented by the general formula [I] and/or [II] and [the above-mentioned (B) and/or the above-mentioned (C)]. In case of an olefin polymerization catalyst prepared by using the transition metal compound (A) and the above-mentioned (B), the fore-mentioned cyclic aluminoxane (B2) and/or the linear aluminoxane (B3) is preferable as (B). Further, as another preferable mode of an olefin polymerization catalyst, an olefin polymerization catalyst prepared by using the transition metal compound, (A), the above-mentioned (B) and the above-mentioned (C) is illustrated, and the fore-mentioned (B1) is also easily used as said (B).

In the present invention, the transition metal compound (A) represented by the general formula [I] and/or [II] and the above-mentioned (B), or further the above-mentioned (C) can be charged in an arbitrary order during polymerization to be used, but a reaction product obtained by previously contacting an arbitrary combination of those compounds may be also used.

The used amount of respective components is not specifically limited, and it is desirable to usually use the respective components so that the molar ratio of the (B)/ transition metal compound (A) is 0.1 to 10000 and preferably 5 to 2000, and the molar ratio of the (C)/transition metal compound (A) is 0.01 to 100 and preferably 0.5 to 10.

When the respective components are used in a solution condition or a condition in which they are suspended or slurried in a solvent, the concentration of the respective components is appropriately selected according to the conditions such as the ability of an apparatus for feeding the respective components in a polymerization reactor. The respective components are desirable used so that the concentration of the transition metal compound (A) is usually 0.001 to 200 mmol/L, more preferably 0.001 to 100 mmol/L and most preferably 0.05 to 50 mmol/L; the concentration of (B) is usually 0.01 to 5000 mmol/L converted to Al atom, more preferably 0.1 to 2500 mmol/L and most preferably 0.1 to 2000 mmol/L; and the concentration of (C) is usually 0.001 to 500 mmol/L, more preferably 0.01 to 250 mmol/L and most preferably 0.05 to 100 mmol/L.

As olefins which can be applied to the polymerization in the present invention, olefins having 2 to 20 carbon atoms such as, particularly, ethylene and an α-olefin having 3 to 20 carbon atoms, diolefins having 4 to 20 carbon atoms and the like can be used, and two or more monomers can also be used, simultaneously. Specific examples of the olefin include straight-chain olefins such as ethylene, propylene, butene-1, pentene-1, hexene-1, heptene-1, octene-1, nonene-1, decene-1 and the like; branched olefins such as 3-methylbutene-1, 3-methylpentene-1, 4-methylpentene-1, 5-methylhexene-1 and the like; vinylcyclohexane, etc., but the present invention should not be limited to the above-mentioned compounds. Specific examples of the combination of monomers in case of conducting copolymerization include ethylene and propylene, ethylene and butene-1, ethylene and hexene-1, ethylene and octene-1, propylene and butene-1 and the like, but the present invention should not be limited thereto.

The present invention can be effectively applied to the particular preparation of the copolymer of ethylene and an α-olefin such as in particular, propylene, butene-1, 4-methylpentene-1, hexene-1, octene-1 or the like.

Polymerization processes should not be also specifically limited, and there can be a solvent polymerization or slurry polymerization in which an aliphatic hydrocarbon such as butane, pentane, hexane, heptane, octane or the like; and aromatic hydrocarbon such as benzene, toluene or the like; or a halogenated hydrocarbon such as methylene dichloride or the like used as a polymerization medium. Further, high pressure ionic polymerization in which the polymerization of an olefin is conducted without a solvent under which an olefin polymer is melt in a high temperature and high pressure olefin in a supercritical liquid condition, and further, a gas phase polymerization in a gaseous monomer and the like are possible. Further, either of a continuous polymerization and a batch-wise polymerization are possible.

The polymerization temperature can be usually adopted at a range of 31 50° C. to 350° C. and preferably 0° C. to 300°

C., and in particular, a range of 50° C. to 300° C. is preferable. The polymerization pressure can be adopted at a range of atmospheric pressure to 350 MPa and preferably atmospheric pressure to 300 MPa, and in particular, a range of atmospheric pressure to 200 MPa is preferable.

In general, the polymerization time is appropriately determined according to the kind of a desired polymer and a reaction apparatus, and the conditions are not specifically limited and a range of 1 minute to 20 hours can be adopted. Further, a chain transfer agent such as hydrogen or the like can also be added to adjust the molecular weight of a copolymer in the present invention.

The process for polymerizing the olefin polymer of the present invention is suitably carried out by a high-pressure ionic polymerization process, in particular.

Specifically, it is preferably carried out under a pressure of 30 MPa or more and at a temperature of 300° C. or more. It is more preferably carried out under a pressure of 35 to 350 MPa and at a temperature of 135 to 350° C.

The polymerization form can be carried out in either a batch-wise manner or a continuous manner, but the continuous manner is preferable. As a reactor, a stirring vessel type reactor or a tubular reactor can be used. The polymerization can be performed in a single reaction zone. Alternatively, the polymerization can also be performed by partitioning one reactor into a plurality of reaction zones or connecting a plurality of reactors in series or parallel. In case of using a plurality of reactors, a combination of a vessel reactor and a vessel reactor or a combination of a vessel reactor and a tubular reactor may be used. In a polymerization process using a plurality of reaction zones or a plurality of reactors, polymers having different characteristics can also be produced by changing the temperature, pressure and gas composition of respective reaction zones or reactors.

EXAMPLE

The present invention is further illustrated in detail according to Examples and Comparative Examples below, but the present invention is not limited thereto.

Properties of the polymers in Examples were measured according to methods described below.

(1) Melt index (MFR) was measured at 190° C. according to the method defined in JIS K-6760. (Unit: g/10 min.)

(2) Density was determined according to JIS K-6760.

Wherein the value of density described as density (without annealing) is a value obtained by measuring without an annealing treatment in JIS K-6760. (Unit: g/cm$^3$)

(3) Melting point of copolymer: It was measured under the following conditions using DSC7 manufactured by Perkin-Elmer Co.

Heating: heating to 150° C. and maintaining until the change of calorie is stabilized Cooling: 150 to 10° C. (5° C./min.) and maintaining for 10 minutes Measurement: 10 to 160° C. (5° C./min.)

(4) Content of 60-olefin:

It was determined from the characteristic absorption of ethylene and 60-olefin using an infrared spectrometer (FT-IR7300, manufactured by NIPPON BUNKO Inc.) and was represented as a short-chain branch (SCB) number per 1000 carbon atoms.

(5) Weight average molecular weight (Mw), number average molecular weight (Mn) and molecular weight distribution (Mw/Mn):

They were determined under the following conditions using gel permeation chromatography (150, c, manufactured by Waters Co.).

Column: TSK gel GMH-HT

Measurement temperature: set at 145° C.

Measurement concentration: 10 mg/10 ml ortho-dichlorobenzene (6) Intrinsic viscosity ([η]):

100 mg of a copolymer obtained was dissolved in 50 ml of tetralin at 135° C. and the solution was set in an oil bath maintained at 135° C. Using an Ubbelohde viscometer, the intrinsic viscosity was determined by the falling speed of the tetralin solution in which said sample was dissolved. (Unit: dl/g)

REFERENCE EXAMPLE 1

[Synthesis of transition metal compound: dimethylsilylene($\eta^5$-tetramethylcyclopentadienyl) (3-tert-butyl-5-methyl-2-phenoxy) titanium dimethoxide)]

In a Schlenk tube, 0.131 g (4.1 mmol) of methanol was dissolved in 10 ml of anhydrous diethyl ether and a diethyl ether solution (3.9 ml, 4.1 mmol) of methyllithium having a concentration of 1.05 mol/L was added dropwise at −78° C. thereto. The resulting mixture was heated to 20° C., the formation of lithium methoxide was confirmed by gas generation, and the resulting reaction solution was again cooled to −78° C. Into the reaction solution, 20 ml of an anhydrous diethyl ether suspension liquid of 0.919 g (2.0 mmol) of dimethylsilylene ($\eta^0$-tetramethylcyclopentadienyl) (3-tert-butyl-5-methyl-2-phenoxy) titanium dichloride which was previously prepared in another Schlenk tube was transferred, and then, the resulting reaction mixture was gradually heated to room temperature to obtain a reaction solution. After concentrating the reaction solution, 20 ml to toluene was added and an insoluble product was separated by filtration. The filtrate was concentrated to obtain dimethylsilylene($\eta^5$-tetramethylcyclopontadienyl) (3-tert-butyl-5-methyl-2-phenoxy) titanium dimethoxide of yellow crystals (0.86 g, 95%).

[1] NMR (270 MHz, $C_4D_5$); δ7.26 (m, 2 H), 4.13 (s, 6 H), 2.33 (s, 3 H), 1.97(s, 6 H), 1.89(s, 6 H), 1.59(s, 9 H), 0.55(s, 6 H)

REFERENCE EXAMPLE 2

[Synthesis example of transition metal compound: μ-oxobis {dimethylsilylene ($\eta^5$-tetramethyl cyclopentadienyl) (3-tert-butyl-5-methyl-2-phenoxy) titanium methoxide (Compound 1)}

Under a nitrogen atmosphere, 10.00 g of dimethylsilylene ($\eta^5$-tetramethylcyclopentadienyl) (3-tert-butyl-5-methyl-2-phenoxy) titanium dimethoxide (the compound obtained by the same method as in Reference Example 1) was dissolved in 50 ml of heptane, 0.30 g of distilled water was added thereto, and the mixture was stirred at the same temperature for 12 hours. The solid produced was separated by filtration, rinsed with 5.0 ml of heptane, and then dried under vacuum to obtain μ-oxobis{dimethylsilylene($\eta^5$-tetramethyl cyclopentadienyl) (3-tert-butyl-5-methyl-2-phenoxy) titanium methoxide} of a yellow solid (5.51 g, 56%).

Mass spectrum (m/c) 855 Calculated value: 855

$^1$H-NMR ($C_4D_4$); δ7.25 (d, J-2.0 Dz, 2 H), 7.16 (d, J=2.0 Hz, 2 H), 3.99 (s, 6 H), 2.32 (s, 6 H), 2.30 (s, 6 H), 2.06 (s,

6 H), 1.86 (s, 6 H), 1.71(s, 6 H), 1.27 (s, 18 H), 0.83 (s, 6 H), 0.63 (s, 6 H)

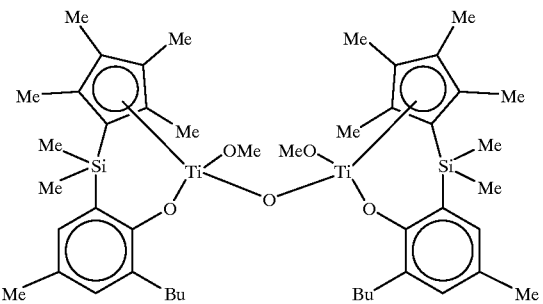

REFERENCE EXAMPLE 3

[Synthesis example of transition metal compound: di-$\mu$-oxobis {dimethylsilylene ($\eta^5$-tetramethyl cyclopentadienyl) (3-tert-butyl-5-methyl-2-phenoxy) titanium} (Compound 2)]

In a Schlenk tube, 1.50 g (3.3 mmol) of dimethylsilylene ($\eta^5$-tetramethylcyclopentadienyl) (3-tert-butyl-5-methyl-2-phenoxy) titanium dimethoxide was dissolved in 20 ml of toluene, 10 ml of water was added thereto, and the resulting liquid mixture was stirred at 70° C. for 1 hour. After concentrating the organic layer which was obtained by phase separation, the concentrate was recrystallized from 10 ml of heptane to obtain di-$\mu$-oxobis {dimethylsilylene($\eta^5$ tetramethyl cyclopentadienyl) (3-tert-butyl-5-methyl-2-phenoxy) titanium} of yellow crystals (0.40 g, 33%). Mass spectrum (m/e) 808. Calculated value: 808

$^1$H-NMR (270 MHz, C$_6$D$_6$); $\delta$7.28 (m, 4 H), 2.32(s, 12 H), 1.97(s, 6 H), 1.78(s, 6 H), 1.59(s, 6 H), 1.53(s, 18 H), 0.78(s, 6 H), 0.58(s, 6 H)

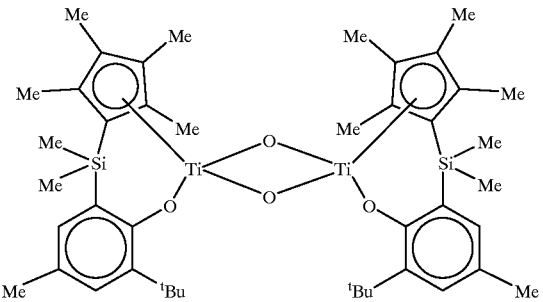

EXAMPLE 1

Using an autoclave type reactor having an inner volume of 1 liter equipped with a stirrer, polymerization was carried out by continuously feeding ethylene and hexene-1 into the reactor. Regarding the polymerization conditions, the total pressure was set to 80 MPa and the concentration of hexene-1 based on the total of ethylene and hexene-1 was set to 28.8% by mole. A heptane solution (which was adjusted to be the concentration of Compound 1 of 0.185 $\mu$mol/g, the concentration of triisobutylaluminum of 18.5 $\mu$mol/g and a molar ratio of Al atom to Ti atom of 50. ) in which $\mu$-oxobis {dimethylsilylene ($\eta^5$-tetramethylcyclopentadienyl) (3-tert-butyl-5-methyl-2-phonoxy) titanium methoxide} (Compound 1) and triisobutylaluminum were mixed and a toluene solution (0.90 $\mu$mol/g) of N,N-dimethylaniliniumtetrakis (pentafluorophenyl)borate were respectively prepared in separate vessels. Each of the solutions was continuously fed in the reactor at a feeding rate of 100 g/hour and 140 g/hour. The polymerization reaction temperature was set at 222° C., and a molar ratio of boron atom to Ti atom was set to 3.4. As a result, an ethylene-hexene-1 copolymer having MFR of 8.39, a density (without annealing) of 0.883 g/cm$^3$, SCB of 36.0, a weight average molecular weight (Mw) of 62000 and a molecular weight distribution (Mw/Mn) of 1.9 was produced at a rate of 74 ton per 1 mole of Ti atom.

COMPARATIVE EXAMPLE 1

Using an autoclave type reactor having an inner volume of 1 liter equipped with a stirrer, polymerization was carried out by continuously feeding ethylene and hexene-1 into the reactor. The total pressure was set to 80 MPa and the concentration of hexene-1 based on the total of ethylene and hexene-1 was set to 34% by mole. A hexane solution (0.7 $\mu$mol/g) of dimethylsilylene ($\eta^5$-tetramethylcyclopentadienyl) (3-tert-butyl-5-methyl-2-phenoxy) titanium dichloride, a heptane solution of triisobutylaluminum (33 $\mu$mol/g) and further a toluene solution (1.2 $\mu$mol/g) of N,N-dimethylaniliniumtetrakis (pentafluorophenyl)borate were respectively prepared in separate vessels and continuously fed into the reactor at feeding rates of 290 g/hour, 350 g/hour and 580 g/hour, respectively. The polymerization reaction temperature was set at 215° C., and a molar ratio of boron atom to Ti atom was set to 3.3. As a result, an ethylene-hexene-1 copolymer having MFR of 4.2, a density (without annealing) of 0.881 g/cm$^3$, a melting point of 67.3° C., SCB of 40.4, Mw of 66000 and Mw/Mn of 1.8 was produced in a rate of 14 ton per 1 mole of Ti atom.

EXAMPLE 2

After replacing the atmosphere of an autoclave type reactor having an inner volume of 0.4 liter equipped with a stirrer with argon, 185 ml of cyclohexane as a solvent and 15 ml of hexene-1 as an $\alpha$-olefin were charged and the reactor was heated to 180° C. After the elevation of temperature, ethylene was fed while adjusting at an ethylene pressure of 2.5 Mpa. After the system was stabilized, 0.2 mmol of triisobutylaluminum, 0.5 ml (namely, 0.5 $\mu$mol of Compound 1 and 25 $\mu$mol of triisobutylaluminum) of a heptane solution (which was adjusted to be the concentration of Compound 1 of 1 $\mu$mol/ml, the concentration of triisobutylaluminum of 50 $\mu$mol/ml and a molar ratio of Al atom to Ti atom of 25.) in which $\mu$-oxobis{dimethylsilylene($\eta^5$-tetramethylcyclopentadienyl) (3-tert-butyl-5-methyl-2-phenoxy) titanium methoxide} (Compound 1) and triisobutylaluminum were mixed, were charged and successively, 1.5 $\mu$mol of N,N-dimethylaniliniumtetrakis (pentafluorophenyl)borate was charged as a slurry in heptane. Polymerization was carried out for 2 minutes. As a result of the polymerization, 2.53 g of an ethylene-hexene-1 copolymer having [$\eta$] of 0.85 dl/g, SCB of 31.4 and melting points of 78.6° C. and 90.8° C. was obtained. Polymerization activity per 1 mole of Ti atom was 2.53×10$^6$ g-polymer/mol-Ti atom per 2 minutes.

EXAMPLE 3

After replacing the atmosphere of an autoclave type reactor having an inner volume of 0.4 liter equipped with a stirrer with argon, 185 ml of cyclohexane as a solvent and 15 ml of hexene-1 as an $\alpha$-olefin were charged and the reactor was heated to 180° C. After the elevation of temperature, ethylene was fed while adjusting at an ethylene pressure of 2.5 Mpa. After the inner of system was stabilized, 0.2 mmol of triisobutylaluminum, 0.5 ml (namely, 0.5 $\mu$mol of Compound 1 and 25 $\mu$mol of triisobutylaluminum) of a heptane solution (which was adjusted to be the concentration of Compound 1 of 1 μmol/ml, the concentration of triisobutylaluminum of 50 μmol/ml and a molar ratio of Al atom to Ti atom of 25.) in which μ-oxobis{dimethylsilylene($\eta^5$-tetramethylcyclopentadienyl) (3-tert-butyl-5-methyl-2-phenoxy) titanium methoxide } (Compound 1) and triisobutylaluminum were mixed, were charged and successively, 3 μmol of N,N-dimethylanilinium tetrakis (pentafluorophenyl)borate was charged as a slurry in heptane (a slurry concentration of 1 μmol/ml). Polymerization was carried out for 2 minutes. As a result of the polymerization, 5.33 g of an ethylene-hexene-1 copolymer having [η] of 0.67 dl/g, SCB of 35.0, melting points of 74.2° C. and 88.6° C., Mw of 43000 and Mw/Mn of 2.7 was obtained. Polymerization activity per 1 mol of Ti atom was 5.33×10$^6$ g-polymer/mol-Ti atom per 2 minutes.

EXAMPLE 4

After replacing the atmosphere of an autoclave type reactor having an inner volume of 0.4 liter equipped with a stirrer with argon, 185 ml of cyclohexane as a solvent and 15 ml of hexene-1 as an α-olefin were charged and the reactor was heated to 180° C. After the elevation of temperature, ethylene was fed while adjusting at an ethylene pressure of 2.5 Mpa. After the system was stabilized, 0.2 mmol of triisobutylaluminum, 0.5 ml (namely, 0.5 μmol of Compound 2 and 25 μmol of triisobutylaluminum) of a heptane solution (which was adjusted to be the concentration of Compound 2 of 1 μmol/ml, the concentration of triisobutylaluminum of 50 μmol/ml and a molar ration of Al atom to Ti atom of 25.) in which di-μ-oxobis{dimethylsilylene($\eta^5$-tetramethylcyclopentadienyl) (3-tert-butyl-5-methyl-2-phenoxy) titanium} (Compound 2) and triisobutylaluminum were mixed, were charged and successively, 1.5 μmol of N,N-dimethylanilinium tetrakis(pentafluorophenyl)borate was charged as a slurry in heptane (a slurry concentration of 1 μmol/ml). Polymerization was carried out for 2 minutes. As a result of the polymerization, 2.55 g of an ethylene-hexene-1 copolymer having [η] of 0.84 dl/g, SCB of 30.7 and melting points of 80.2° C. and 93.0° C. was obtained. Polymerization activity per 1 mole of Ti atom was 2.55 ×10$^6$ g-polymer/mol-Ti atom per 2 minutes.

EXAMPLE 5

After replacing the atmosphere of an autoclave type reactor having an inner volume of 0.4 liter equipped with a stirrer with argon, 185 ml of cyclohexane as a solvent and 15 ml of hexene-1 as an α-olefin were charged and the reactor was heated to 180° C. After the elevation of temperature, ethylene was fed while adjusting at an ethylene pressure of 2.5 Mpa. After the system was stabilized, 0.2 mmol of triisobutylaluminum, 0.5 ml (namely, 0.5 μmol of Compound 2 and 25 μmol of triisobutylaluminum) of a heptane solution (which was adjusted to be the concentration of Compound 2 of 1 μmol/ml, the concentration of triisobutylaluminum of 50 μmol/ml and a molar ratio of Al atom to Ti atom of 25.) in which di-μ-oxobis{dimethylsilylene($\eta^5$-tetramethylcyclopentadienyl) (3-tert-butyl-5-methyl-2-phenoxy) titanium} (Compound 2) and triisobutylaluminum were mixed, were charged and successively, 3 μmol of N,N-dimethylanilinium tetrakis(pentafluorophenyl)borate was charged as a slurry in heptane (a slurry concentration of 1 μmol/ml). Polymerization was carried out for 2 minutes. As a result of the polymerization, 3.92 g of an ethylene-hexene-1 copolymer having [η] of 0.73 dl/g, SCB of 33.0, melting points of 78.9° C. and 91.5° C., Mw of 48000 and Mw/Mn of 2.5 was obtained. Polymerization activity per 1 mole of Ti atom was 3.92×10$^6$ g-polymer/mol-Ti atom per 2 minutes.

As described above in detail, according to the present invention, a transition metal compound useful as a highly active olefin polymerization catalyst component at an efficient reaction temperature in the industrial process of an olefin polymerization, and a highly active olefin polymerization catalyst using said transition metal compound and a process of producing an olefin polymer using said olefin polymerization catalyst are provided. Further, the transition metal compound of the present invention is also effective as an olefin polymerization catalyst component having a high comonomer reaction rate in copolymerization and providing an olefin polymer with a high molecular weight, and has a remarkable value for utilization.

What is claimed is:

1. A transition metal compound represented by the general formula [I] or [II] described below:

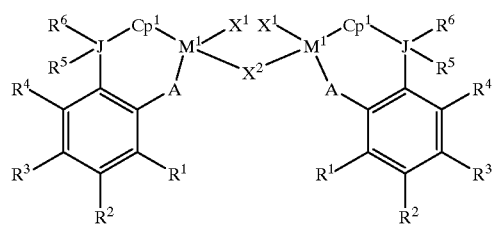

[I]

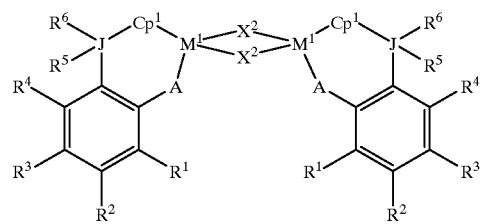

[II]

wherein $M^1$ is a transition metal atom of the Group IV of the Periodic Table of the Elements; A is an atom of the Group XVI of the Periodic Table of the Elements; J is an atom of the Group XIV of the Periodic Table of the Elements; $Cp^1$ is a group having a cyclopentadiene type anion skeleton; each of $X^1$, $R^1$, $R^2$, $R^3$, $R^4$, $R^5$ and $R^6$ independently is a hydrogen atom, a halogen atom, an alkyl group, an aralkyl group, an aryl group, a substituted silyl group, an alkoxy group, an aralkyloxy group, an aryloxy group or a di-substituted amino group; $X^2$ is an atom of Group XVI of the Periodic Table of the Elements; $R^1$, $R^2$, $R^3$, $R^4$, $R^5$ and $R^6$ may be optionally combined with each other to form a ring; and a plural number of $M^1$, A, J, $Cp^1$, $X^1$, $X^2$, $R^1$, $R^2$, $R^3$, $R^4$, $R^5$ and $R^6$ may be respectively the same or different.

2. The transition metal compound according to claim 1, wherein said A is an oxygen atom.

3. The transition metal compound according to claim 1, wherein said $X^2$ is an oxygen atom.

4. The transition metal compound according to claim 1, wherein each of said $R^3$ is an alkyl group, an aralkyl group, an aryl group or a substituted silyl group, independently.

5. The transition metal compound according to claim 1, wherein each of said $X^1$ is a halogen atom, an alkyl group, an aralkyl group, an alkoxy group, an aryloxy group or a di-substituted amino group, independently.

* * * * *